United States Patent
Glover et al.

(10) Patent No.: US 7,980,854 B2
(45) Date of Patent: Jul. 19, 2011

(54) DENTAL AND MEDICAL TREATMENTS AND PROCEDURES

(75) Inventors: Douglas L. Glover, Phoenix, AZ (US); Enrico E. DiVito, Scottsdale, AZ (US); Kemmons A. Tubbs, Mesa, AZ (US); Mark P. Colonna, Whitefish, MT (US)

(73) Assignee: Medical Dental Advanced Technologies Group, L.L.C.

( * ) Notice: Subject to any disclaimer, the term of this patent is extended or adjusted under 35 U.S.C. 154(b) by 269 days.

(21) Appl. No.: 12/395,643

(22) Filed: Feb. 28, 2009

(65) Prior Publication Data

US 2009/0220908 A1    Sep. 3, 2009

Related U.S. Application Data

(63) Continuation-in-part of application No. 11/704,655, filed on Feb. 9, 2007, which is a continuation-in-part of application No. 11/895,404, filed on Aug. 24, 2007.

(51) Int. Cl.
*A61C 5/02* (2006.01)
(52) U.S. Cl. .......................... 433/224; 433/29
(58) Field of Classification Search .............. 433/215, 433/216, 224, 29; 606/2–19; 128/898
See application file for complete search history.

(56) References Cited

U.S. PATENT DOCUMENTS

| | | | |
|---|---|---|---|
| 4,676,586 A | 6/1987 | Jones et al. | |
| 4,985,027 A | 1/1991 | Dressel | |
| 5,116,227 A | 5/1992 | Levy | |
| 5,173,049 A * | 12/1992 | Levy | 433/215 |
| 5,188,532 A * | 2/1993 | Levy | 433/216 |
| 5,267,995 A | 12/1993 | Doiron et al. | |
| 5,324,200 A | 6/1994 | Vassiliadis et al. | |
| 5,639,239 A | 6/1997 | Earle | |
| 5,662,501 A | 9/1997 | Yagi | |
| 5,968,039 A | 10/1999 | Deutsch et al. | |
| 6,162,052 A | 12/2000 | Kokobu | |
| 7,470,124 B2 | 12/2008 | Bornstein | |
| 2002/0090594 A1 | 7/2002 | Ritano et al. | |
| 2002/0183728 A1 | 12/2002 | Rosenberg et al. | |
| 2003/0013064 A1 | 6/2003 | Zirkel | |
| 2004/0038170 A1 | 2/2004 | Hirszowicz et al. | |
| 2004/0193236 A1 | 9/2004 | Altshuler | |

* cited by examiner

*Primary Examiner* — Cris L Rodriguez
*Assistant Examiner* — Eric Rosen
(74) *Attorney, Agent, or Firm* — Luedeka, Neely & Graham, P.C.

(57) ABSTRACT

A method treating a root canal in a tooth by introducing into the pulp chamber of a tooth and pulsing a laser light into the fluid reservoir so as to disintegrate pulp within the root canal without generation of any significant heat in said liquid fluid so as to avoid elevating the temperature of any of the dentin, tooth, or other adjacent tissue more than about 5° C.

12 Claims, 5 Drawing Sheets

DENTAL AND MEDICAL TREATMENTS AND PROCEDURES

This application is a continuation-in part of pending application Ser. No. 11/704,655, filed Feb. 9, 2007, and of pending application Ser. No. 11/895,404, filed on Aug. 24, 2007, both of which claim priority to provisional application Ser. No. 60/840,282, filed on Aug. 24, 2006, all of which are incorporated herein by reference.

FIELD OF THE INVENTION

The present invention is related to the field of dentistry, medicine and veterinary medicine.

BACKGROUND OF THE INVENTION

In the field of dentistry, one of the most important and delicate procedures is that of cleaning or extirpating a diseased root canal to provide a cavity which is substantially free of diseased tissue and antiseptically prepared for a permanent embalming or obturation to seal off the area. When done properly, this step enables subsequent substantially complete filling of the canal with biologically inert or restorative material (i.e., obturation) without entrapping noxious tissue in the canal that could lead to failure of the therapy.

In a typical root canal procedure, the sequence is extirpation of diseased tissue and debris from and adjacent the canal followed by obturation. Often there is an intermediate filling of the canal with a calcium hydroxide paste for sterilization and reduction of inflammation prior to obturation and final crowning. In performing the extirpation procedure, the dentist must gain access to the entire canal, shaping it as appropriate. However, root canals often are very small in diameter, and they are sometimes quite curved with irregular dimensions and configurations. It is therefore often very difficult to gain access to the full length of the canal and to properly work all surfaces of the canal wall.

Many tools have been designed to perform the difficult task of cleaning and shaping root canals. Historically, dentists have used elongate, tapered endodontic files with helical cutting edges to remove the soft and hard material from within and adjacent the root canal area. Such root canal dental procedures often result in overly aggressive drilling and filing away of otherwise healthy dentin wall or physical structure of the tooth root, thereby unduly weakening the integrity or strength of the tooth. Additionally, when performing root canal procedures, it is desirable to efficiently debride or render harmless all dead, damaged, or infected tissue and to kill all bacteria, viruses and/or other undesirable biological material within the root canal system. Illustrations of a typical root canal system are shown in FIGS. 1A and 1B. The root canal system includes the main root canal 1 and many lateral or accessory canals 3 that branch off of the main canal 1, all of which can contain diseased or dead tissue, bacteria, etc. It is common during root canal procedure to mechanically strip out the main canal nerve, often tearing it away from the lateral canal nerves, much of which can then stay in place in the canal and become the source of later trouble. Thereafter, the main canal 1 is cleaned and extirpated with a tapered file. While it is desirable to extirpate all of the main and accessory canals in a root canal system, some of the lateral canals 3 are very small and extremely difficult to reach in order to remove tissue. Such lateral canals are often perpendicular to the main canal and may bend, twist, and change cross-section as they branch off from the main canal, making them practically inaccessible to extirpation with any known file or other mechanical device.

Accordingly, lateral canals are often not properly extirpated or cleaned. Many times no effort is made in this regard, relying instead on chemical destruction and embalming processes to seal off material remaining in these areas. This approach is sometimes a source of catastrophic failure that can lead to loss of the tooth and other problems. Further, when the main canal is extirpated with a tapered file, this action can leave an undesirable smear layer along the main canal which can plug some of the lateral canal openings and cause other problems that trap noxious material against later efforts to chemically disinfect the canal.

Dentists can attempt to chemo-mechanically debride and/or sterilize both main and lateral canals using a sodium hypochlorite solution or various other medicaments that are left in the root canal system for 30 to 45 minutes a time following primary mechanical extirpation of nerve and pulp tissue. However, this approach does not necessarily completely debride or render harmless all of the lateral root canals and material trapped therein because of the difficulty in cleaning off the smear layer and/or negotiating and fully wetting the solution into some of the smaller twisted lateral canals. As a result, many treatments using this method fail over time due to reoccurring pathology. This often requires retreatment and sometimes loss of the tooth.

Attempts have been made to reduce or eliminate the use of endodontic files and associated drawbacks by using lasers in the performance of root canal therapy. Some of these approaches involve burning away or carbonizing diseased and other tissue, bacteria, and the like within the canal. In these approaches, laser light is said to be directed or focused into or onto the diseased tissue, producing very high temperatures that intensely burn, carbonize, ablate, and destroy the tissue. These ablative treatments using high thermal energy to remove tissue often result in damage to the underlying collagen fibers and dentin of the root 5, even fusing the hydroxyapatite which makes up the dentin. In some cases, such treatments can cause substantial heating of the periodontal material and bone 7 surrounding the tooth, potentially causing necrosis of the bone and surrounding tissue. Additionally, the high temperatures in such treatments can melt the walls of the main canal, often sealing off lateral canals, thereby preventing subsequent treatment of lateral canals. Other attempts to use lasers for root canal therapy have focused laser light to a focal point within fluid disposed within a root canal to boil the fluid. The vaporizing fluid creates bubbles which erode material from the root canal when they implode. Such treatments which must raise the fluid temperature above the latent heat of vaporization significantly elevate the temperature of the fluid which can also melt portions of the main canal and cause thermal damage to the underlying dentin, collagen, and periodontal tissue. The damage caused to the tooth structure by these high energy ablative laser treatments weakens the integrity or strength of the tooth, similar to endodontic treatment utilizing endodontic files.

Therefore, there is a present and continuing need for minimally invasive, biomemetic, dental and medical therapies which remove diseased tissue and bacteria from the main root canal as well as the lateral canals of the root canal system while leaving the biological structures undamaged and substantially intact.

SUMMARY OF INVENTION

In accordance with one embodiment of the present invention, a method is provided for treating a root canal in a tooth containing a crown portion extending to above a gum line and one or more elongate roots integral with and projecting from the crown into the gum and an adjacent jaw bone. Each root has a root canal containing pulp including nerve and other tissue in open communication with a pulp or coronal chamber in the crown. An opening is formed in the crown into the pulp chamber dimensioned to enable working access to a canal of said one or more roots for treatment thereof. Pulp is removed from the pulp chamber to provide an open area therein to gain access to pulp in said canal and, optionally, remove at least part of the pulp from said canal to make an opening in said canal in flow communication with said open area in said pulp chamber. Liquid containing hydroxyl groups is dispensed into at least the open area in the pulp chamber in an amount sufficient to provide a liquid reservoir.

A laser system is provided containing a source of a laser light beam and an elongate optical fiber connected to said source and configured to transmit said laser light beam to a tip portion thereof. The tip may include a tapered tip tapering to an apex with a surrounding conical wall, substantially the entire surface of which is uncovered so that said laser light beam is emitted therefrom generally omnidirectionally. The optical fiber may also contain cladding in the form of a continuous sheath coating extending from the source to a terminus edge spaced proximally from said apex of said tapered tip toward said source by a distance of from about 2 to about 10 millimeters so that the surface of said optical fiber is uncovered over the entirety of said tapered tip and over any part of a cylindrical outer surface of the fiber between the terminus and the beginning of the tapered end.

The tip of the laser is substantially completely immerse into the liquid reservoir, and pulsing said laser source at a power level of from about 0.1 W to about 1.5 W and at a pulse duration of from about 50 to about 1000 microseconds, at a pulse frequency of from about 2 Hz to about 25 Hz, and for a cycle time of from about 10 to about 40 seconds.

DETAILED DESCRIPTION OF THE DRAWINGS

FIGS. 1a and 1b illustrate a root canal system including a main or primary root canal and lateral and sub-lateral canals that branch off of the main canal. Some of these lateral canals are very small and extremely difficult to reach in order to eliminate any bacteria and/or viruses. Such lateral canals may bend, twist, change cross-section and/or become long and small as they branch off from the main canal, making them very difficult to access or target therapeutically.

FIG. 2 is a Scanning Electron Micrograph (SEM) clearly illustrating internal reticular canal wall surfaces following use of the present invention which, as can be seen, are preserved with no burning, melting, or other alteration of the canal wall structure or loss of its porosity after subtraction of the internal tissue. The surfaces retain high porosity and surface area and are disinfected for subsequent filling and embalming, i.e. using rubber, gutta-percha, latex, resin, etc.

DESCRIPTION OF THE PREFERRED EMBODIMENTS

Figure 1A:
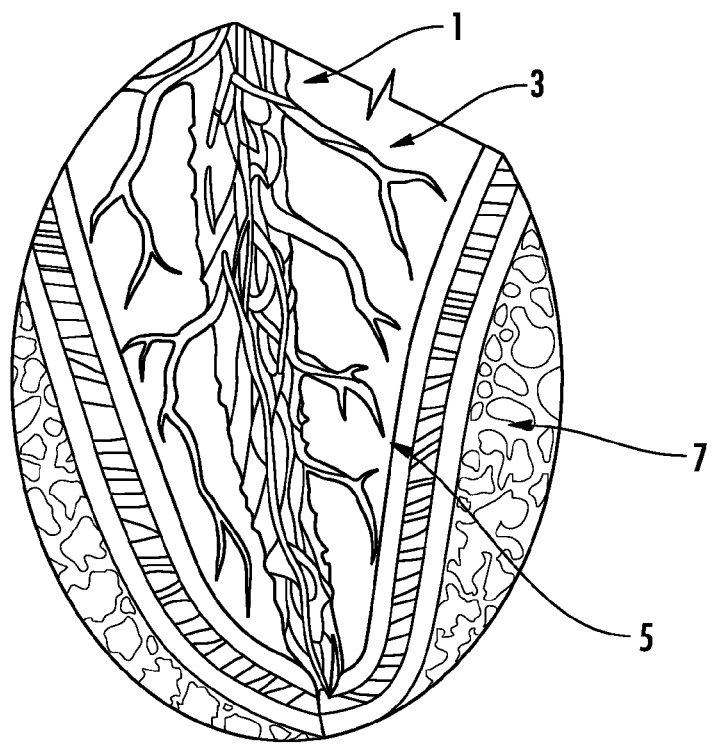
Figure 1B:
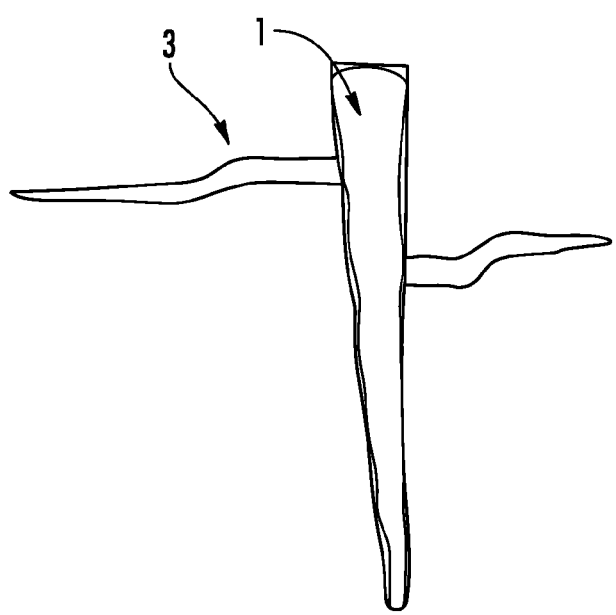
Figure 2:
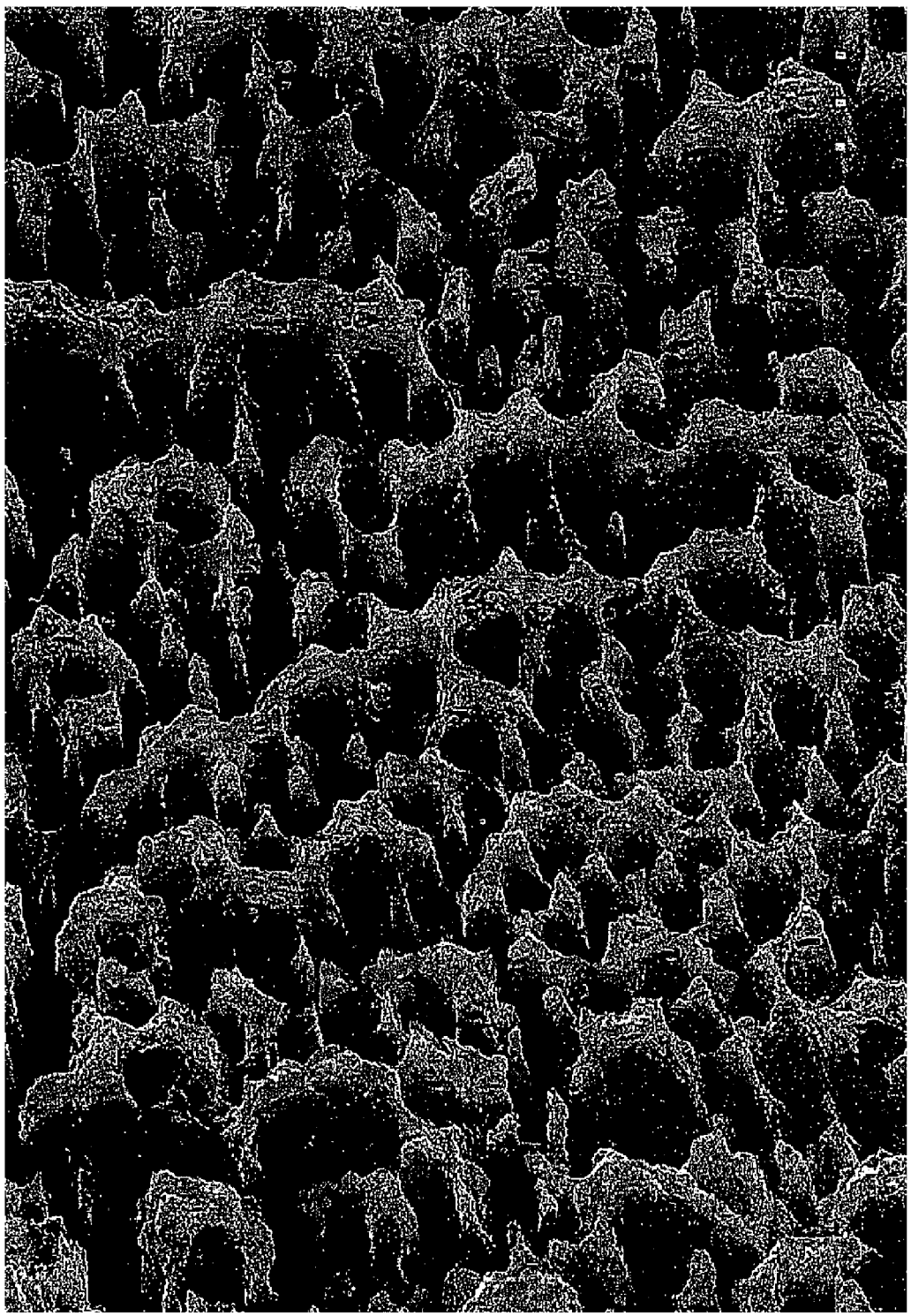
Figure 3:
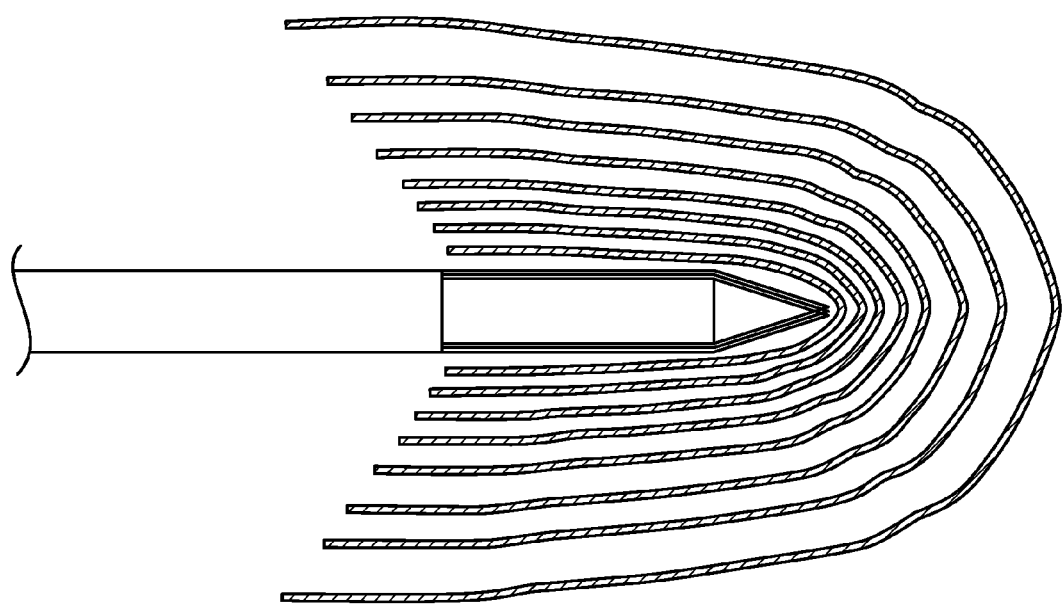
FIG. 3 is a graphical illustration of features of a laser fiber tip configured according to a preferred embodiment of the present invention.
Figure 4:
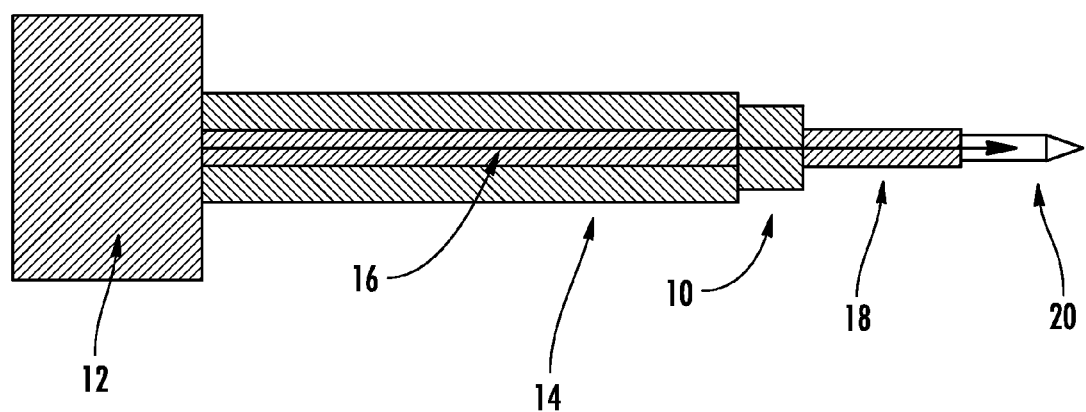
FIG. 4 is a graphical illustration of a laser system according to an embodiment of the present invention.
Figure 5:
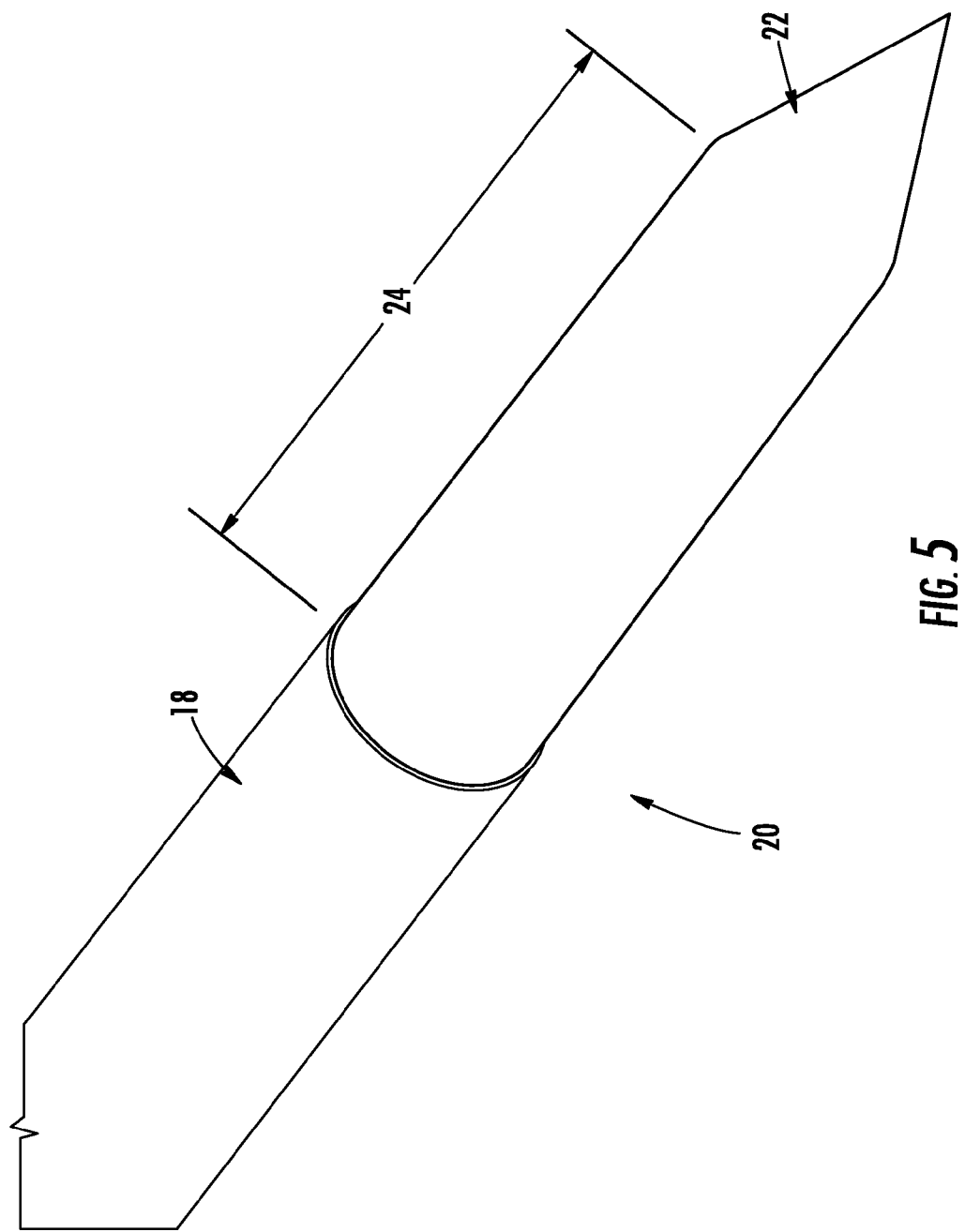
FIG. 5 is a graphical illustration of an applicator tip of a laser system according to an embodiment of the invention.

A method and apparatus according to a preferred embodiment of the present invention uses a subablative energy source, preferably a pulsing laser, to produce photoacoustic energy waves in solutions dispensed in a root canal to effectively clean the root canal and lateral canals. In the context of this application, the term "subablative" is used to refer to a process or mechanism which does not produce or cause thermal energy-induced destruction of nerve or other native tooth structure, material or tissue, namely, that does not carbonize, burn, or thermally melt any tooth material. The pulsing laser in the inventive configuration of a preferred embodiment induces oscillating photoacoustic energy waves which emanate generally omnidirectionally from adjacent the exposed length of an applicator tip where light energy is caused to exit the surface of optical fiber material in many directions/orientations into adjacent fluid medium from a light energy source maintained at a relatively low power setting of from about 0.1 to no more than about 1.5 watts in order to avoid any ablative effects.

According to one embodiment of the present invention, a tooth is first prepared for treatment in a conventional manner by drilling a coronal access opening in the crown of the tooth to access the coronal or pulp chamber and associated root canal. This may be performed with a carbide or diamond bur or other standard approaches for preparation of a tooth for root canal treatment known in endodontic practice after which the upper region above the entry of the canal into the chamber is generally emptied of pulp and other tissue. Thereafter, a first solution is slowly dispensed into the chamber, such as by use of a syringe or other appropriate mechanisms, with a small amount seeping and/or injected down into the individual root canals containing the as-yet unremoved nerves and other tissue. The first solution is preferably dispensed in an amount sufficient to fill the chamber to adjacent the top of the chamber. In other embodiments, portions of the nerve and other tissue in the canals may be removed using a broach or other known methods for removing a nerve from a root canal before the first solution is dispensed into the chamber and down into the root canals. In some embodiments, only a single solution may be used, although multiple solutions or mixtures may also be used as explained in more detail below.

The first solution preferably includes a compound containing molecules with at least one hydroxyl functional group and/or other excitable functional groups which are susceptible to excitation by a laser or other energy source in the form of rapidly oscillating photoacoustic waves of energy to assist with destructive subablative disintegration of root canal nerve tissue. It has been observed that certain fluids which do not contain excitable groups, such as xylene, do not appear to produce the desired photoacoustic wave when an energy source has been applied. In one embodiment of the invention, the first solution is a standard dental irrigant mixture, such as a solution of water and ethylenediamine tetraacetic acid (EDTA), containing hydroxyl or other excitable groups. In other embodiments of the invention, the hydroxyl-containing solution may be distilled water alone. In other alternate embodiments, solutions containing fluids other than water may be used, or various pastes, perborates, alcohols, foams, chemistry-based architectures (e.g. nanotubes, hollow spheres) and/or gels or a combination of the like may be used. Additionally, various other additives may be included in the solution. For example, and not by way of limitation, the first solution may include agents energizable by exposure to energy waves propagated through the solution from adjacent the fiber. These include materials selected from the group consisting of hydrogen peroxide, perborates, hypochlorites, or other oxidizing agents and combinations thereof. Additional additives believed to be energizable in the solution include materials selected from the group consisting of reducing agents, silanols, silanating agents, chelating agents, chelating agents coordinated or complexed with metals (such as EDTA-Calcium), anti-oxidants, sources of oxygen, sensitizing agents, catalytic agents, magnetic agents and rapidly expanding chemical, pressure or phase change agents and/or combinations of the like. The solution may also include dispersions or mixtures of particles containing nano- or microstructures, preferably in the nature of fullerenes, such as nanotubes or bucky balls, or other nanodevices (including micro-sized devices) capable of sensitizing or co-acting with oxygenating, energizable, or activatable components in the solution/mixture, such as oxidative bleaching or other oxygenated agents. Various catalytic agents may be titanium oxide or other similar inorganic agents or metals. The first solution may also include additional effective ingredients such as surfactants or surface active agents to reduce or otherwise modify the surface tension of the solution. Such surface active agents may be used to enhance lubrication between the nerves and other intracanal tissue and the canals wall, as well as antibiotics; stabilizers; antiseptics; anti-virals; germicidals; and polar or non-polar solvents; and the like. It is especially preferred that all materials used in the system be bio-compatible and FDA and otherwise approved, as necessary, for use in dental procedures. The amounts of any of the foregoing and other additives are generally very small in the order of a few percent by weight or only small fractions of percents. The majority of the solution/mixture is preferably water, preferably sterile triple distilled water for avoidance of undesirable or unaccounted for ionic effects.

An activating energy source is applied to the first solution contained in the coronal pulp chamber. In a preferred embodiment, the activating energy source is a pulsing laser 10. The laser light energy 16 is delivered using a laser source 12 and an optical light fiber 14 attached at its proximate end to a laser source 12 and having an applicator tip 20 adjacent its distal end. The optical fiber 14 preferably has a diameter of from about 200 microns to about 400 microns. The diameter should be small enough to easily fit into the coronal pulp chamber and, if necessary, into a root canal itself, but large enough to provide sufficient energy via light carried therein to create a photoacoustic effect and to prevent avoidable leakage of light or loss of energy and damage to the tooth or the fiber tip. In a preferred embodiment, the laser source is a solid state laser having a wavelength of from about 700 nm to about 3000 nm, such as NdYAG, ErYAG, HoYag, NdYLF, Ti Sapphire, or ErCrYSGG laser. However, other suitable lasers sources may be used in various embodiments.

An appropriately dimensioned laser applicator tip 20 is preferably placed into the coronal chamber until it is at least fully immersed in the first solution. By "fully immersed" it is meant liquid level is even with the edge of the cladding or other covering on the optical fiber 14. Preferably, the distal most edge of any cladding or covering 18 on the optic fiber 14 adjacent the tip is spaced approximately 2-10 mm from the distal end of the distal end tip or end of the fiber, most preferably about 5 mm therefrom. As a result, up to about 10 mm and most preferably about 5 mm of the distal end of the fiber is uncovered. Preferably, all or substantially all of the length of this uncovered part of the tip end is immersed. If the uncovered part of the applicator tip is not fully immersed, sufficient energy may not be transferred to the fluid since light will be permitted to escape to the environ above the liquid surface. Accordingly, it is believed that spacing the distal-most or outermost end edge of the cladding more than about 10 mm should be avoided, as that can diminish the effectiveness of the system. In some applications, it may be necessary to provide a dam and reservoir around and above the opening in the tooth in order to increase the volume and level of fluid available for immersion of the uncovered area of the end of the fiber. The larger liquid volume and deeper immersion of the uncovered area of the tip end is believed to enable application of sufficient energy levels to produce the desired photoacoustic wave intensity in such instances. Such instances may include, for example, smaller teeth such as upper/lower centrals or teeth that are fractured off. In certain applications where a dam or reservoir is used it may be desirable to use a laser tip with more than 10 mm of space between the tip end and the cladding due to the larger volume of fluid.

It is a feature of the invention in a preferred embodiment that the distal-most end of the applicator tip be tapered to and end point, i.e. that the distal end have a "tapered tip" 22. Most preferably, the tapered tip has an included taper angle of from about 25 to about 40 degrees. The applicator tip 20 is therefore preferably not a focusing lens configured to concentrate light to a point in space away from the tip end. Such a configuration is believed to cause an ablative effect due to the high thermal energy created by the laser light focused to a point. Rather, the taper angle of the tapered fiber tip 22 and rearward spacing of the end of the cladding from the tip end in accordance with preferred embodiments of the invention are believed to enable a relatively wide dispersion of the laser energy for emission from a relatively large surface area of the tip all the way back to the edge of the cladding, not merely from the end of the laser fiber. An objective is to emit laser light generally omnidirectionally from the sides 24 and from the tapered area of the tapered tip 22, and consequently, to produce a larger or more omnidirectional photoacoustic wave propagating into surrounding liquid and adjacent material from substantially the entire exposed surface of the fiber optic quartz material. Among other things, this avoids and preferably eliminates any ablative effects associated with higher levels of focused or refracted radiant laser energy. The tip design in accordance with the invention is selected to provide a magnitude and direction of the photoacoustic wave in the surrounding fluid medium that exhibits a relatively sharp or high rise time at the leading edge of each pulse and which propagates through the fluid generally omnidirectionally from the exposed area of the end of the fiber. Accordingly, a tapered tip according to the invention has the effect of dispersing the laser energy over the larger uncovered cone surface area and the rearwardly extending cylindrical wall surface (compared to a two dimensional generally flat circular surface area of a standard tip), thereby creating a much larger area through which the leading edges of the successive photoacoustic waves can propagate. In some embodiments, the exposed area of the fiber adjacent the tip end may include a texturing, such as frosting or etching, to increase the surface area and angular diversity of light emission for an even more comprehensive coverage of the photoacoustic wave energy within the solution and adjacent tissue.

When applying the laser to the first solution, applicants have discovered that it may be important to apply the laser energy to the solution so as to limit the creation of thermal energy. In the present invention, after the applicator tip is immersed in the first solution, laser energy is preferably applied to the first solution using subablative threshold settings, thereby avoiding any thermal-induced carbonization, melting, or other effects caused by a temperature rise above about 5° C. in the dentin walls of the canal, apical portions of the tooth, or surrounding bone or tissue caused by the generation of significant thermal energy in the canal area or wall due to the ablative power settings used in prior attempts to perform root canal therapy with lasers. The practice of the present invention in accordance with its preferred embodiments causes an observable temperature rise in the solution of no more than a few degrees Centigrade and, as a result, no more than a few degrees Centigrade elevation, if any, of the dentin wall and other adjacent tooth structure and tissue. This is far below the standard constraint of avoiding any exposure of such material and tissue to more than 5° C. increase in temperature for any significant period of time to avoid permanent damage in the same.

The inventors have found that relatively low power settings of from about 0.1 watt to about 1.5 watt and with a laser pulse duration of from about 100 nanoseconds to about 1000 microseconds, with a pulse length of about 50 microseconds most preferred, produces the desired photoacoustic effect without heating the fluid or surrounding tissue to produce any ablative or other thermal effect within or adjacent the root canal. A frequency of from about 5 to 25 Hz is preferred and a frequency of about 15 Hz is believed to provide optimal potentiation of harmonic oscillation of pressure waves in the fluid medium to disintegrate nerve and other tissue within the canal.

The particular preferred power level found to produce the ideal photoacoustic wave has a relationship to the approximate root volume of a particular tooth. The following chart (Table 1) shows what are believe to be preferred ranges of power levels for treatment of root canals in different types and sizes of teeth in accordance with the invention.

TABLE 1

Preferred Power Levels for Various Tooth Types

| Tooth Type | Approx. Average Root Volume (µL) | Range of Preferred Power Levels (watts) |
|---|---|---|
| Molar | 177 | 0.5 to 1.5 |
| Pre Molar | 88 | 0.5 to 1.0 |
| Cuspid | 67 | 0.5 to 0.75 |
| Laterals | 28 | 0.25 to 0.5 |
| Centrals | 28 | 0.25 to 0.5 |
| Lower Centrals | 28 | 0.1 to 0.25 |

When the laser is immersed in the first solution, the laser is pulsed for a time preferably ranging from about 10 seconds to about 40 seconds, most preferably about 20 seconds. If the laser is pulsed for longer than about 40 seconds, excessive thermal energy can begin to develop in the fluid, potentially leading to deleterious heating effects in and around the tooth as described above. It has been found rather surprisingly that pulsing under the parameters of the invention causes a measurable temperature rise in the fluid medium of no more than a few degrees Celsius, if any, while still utterly destroying and/or disintegrating all nerve, pulp, and other tissue within the canal that also is observed to hydraulically self-eject from the canal during pulsing.

After the laser has been pulsed in the first solution, the first solution is allowed to stabilize and then laser pulsing treatment may be repeated again in the same or a different solution. In certain embodiments, the solution may be removed between repetitions of pulsing cycles of the laser to remove debris more gradually and to avoid any development or transfer of heat energy into the dentin surrounding wall or other adjacent structure. The coronal chamber and canal may be irrigated with a standard dental irrigant and solution may then be reinserted into the coronal chamber to perform an additional laser pulsing treatment. While any number of pulsing phases or cycles can be repeated, it is believed that a fully effective removal of all material within the canal can be achieved in less than about seven cycles.

To assist dentists in performing root canal treatments according to the present invention, a photoacoustic activity index has been developed which provides relationships between the various parameters, machine setting, and the like which have been found to be important in the practice of the inventive procedure. Factors which appear important in the practice of the invention include the power level, laser pulse frequency, the pulse duration, the proportion of average excitable functional groups per molecule in the first solution, the diameter of the laser optical fiber, the number of pulsing cycles repeated in completing an extirpation procedure, the duration of each cycle, the viscosity of the first solution, and the distance between the tip and the end of the cladding. Coefficients have been determined which relate deviations of certain of the above factors from what is believed to be the ideal or the most preferred factor value. Tables of these coefficients are shown below:

| Tooth Type | Approx. Average Root Volume (uL) | Preferred Range of Power Levels (watts) | Power Density Coefficient (DPD) |
|---|---|---|---|
| Molar | 177 | 0.5 to 1.5 | 1 |
| Pre Molar | 88 | 0.5 to 1.0 | 1 |
| Cuspid | 67 | 0.5 to 0.75 | 1 |
| Laterals | 28 | 0.25 to 0.5 | 1 |
| Centrals | 28 | 0.25 to 0.5 | 1 |
| Lower Centrals | 28 | 0.1 to 0.25 | 1 |

| Frequency Coefficient C(fq) | Pulses per Second (Value in HZ) |
|---|---|
| 0.4 | 2 HZ |
| 0.6 | 5 HZ |
| 0.9 | 10 HZ |
| 1 | 15 HZ |
| 0.5 | 20 HZ |
| 0.2 | 25 HZ |

| Pulse Duration Coefficient C(pw) | Pulse Duration Value in micro sec (µs) |
|---|---|
| 1 | <50 |
| 0.9 | 50 |
| 0.7 | 100 |
| 0.3 | 150 |
| 0.2 | 200 |
| 0.1 | 1000 |

| Hydroxyl Coefficient C(hy) | Average quantity of excitable groups per fluid molecule |
|---|---|
| 1 | >2 |
| 0.9 | 2 |
| 0.7 | 1 |
| 0.5 | Part or Mixture |
| 0 | none |

| Fiber Diameter Coefficient C(fd) | Fiber Diameter Value in microns |
|---|---|
| 0.8 | >400 |
| 1 | 400 |
| 0.8 | 320 |
| 0.5 | 200 |
| 0.3 | <200 |

| Repetition Cycle Coefficient C(rp) | Repetition Cycles (repetitions) |
|---|---|
| 0.3 | >7 |
| 0.5 | 6 |
| 0.7 | 5 |
| 1 | 4 |
| 0.9 | 3 |
| 0.6 | 2 |
| 0.3 | 1 |

| Cycle Duration Coefficient C(sa) | Cycle Duration (Value in seconds) |
|---|---|
| 0.2 | >40 |
| 0.6 | 40 |
| 0.9 | 30 |
| 1 | 20 |
| 0.5 | 10 |
| 0.2 | <10 |

| Viscosity Coefficient C(vs) | Fluid Viscosity (Centipoise) |
|---|---|
| 1 | <1 |
| 0.9 | 1 |
| 0.1 | >500 |
| 0.05 | >1000 |

| Cladding Separation Length Coefficient C(sl) | Distance Between Terminus of Cladding and Apex of Tip Value in millimeters (mm) |
|---|---|
| 0.4 | 2 |
| 0.6 | 3 |
| 0.9 | 4 |
| 1 | 5 |
| 0.9 | >5 |
| 0.3 | >10 |

A practitioner may input coefficients from the above tables correlating to equipment, setting, and material parameters into the following equation:

Photoacoustic Activity Index ("PA" Index)=$DPD \times C(fq) \times C(pw) \times C(hy) \times C(fd) \times C(rp) \times C(sa) \times C(vs) \times C(sl)$ If the resulting PA Index value is greater than about 0.1, more preferably above about 0.3, then the equipment and materials may generally be acceptable to produce an effective photoacoustic wave for disintegration and substantially complete and facile removal of all root canal nerve, pulp, and other tissue from within the canal. If the PA Index is below about 0.1, it may indicate a need to modify one's equipment setup, setting, and method parameters in order to more closely approach the desired PA index of 1 or unity.

Using the invention parameters and procedures, root canal tissue and other material to be removed or destroyed is not believed to be removed or destroyed via thermal vaporization, carbonization, or other thermal effect due primarily to exposure to high temperatures, but rather through a photoacoustic streaming of and other activities within liquids in the canal which are laser activated via photon initiated photoacoustic streaming (PIPS). A photoacoustic wave with a relatively high leading edge is generated when the laser light transitions from the exposed surface of the fiber optic material into the solution. The laser light is believed to create very rapid and relatively intense oscillations of waves through the solution emanating from the interface of the exposed surface of the fiber optic and the surrounding liquid. The rapid, intense microfluctuations in the light energy emitted is believed to cause rapid excitation and/or expansion and de-excitation and/or expansion of hydroxyl-containing molecules adjacent the exposed surface of the fiber generating, among other things, photoacoustic waves of energy which propagates through and into the root canal system and oscillates within the system. These intense photoacoustic waves are believed to provide substantial vibrational energy, which expedites the breaking loose of and/or cell lysis and other effects to bring about a rapid and facile degradation/disintegration of substantially all tissue in the root canal and lateral canal systems immersed in the solution. The pulsing photoacoustic energy waves in combination with the chemistry of the fluid also is believed to cause intense physically disruptive cycling of expanding and contracting of nerve and other tissue which porositizes, expands, and ultimately disintegrates the nerve and other tissue in the canal without any significant thermally induced carbonization or other thermal effects of the same so that the resulting solution/mixture containing nerve and other tissue remains is observed to be self-ejected or basically "pumped" by a hydraulic effect out of the canal.

The photoacoustic effect creates energy waves that propagate throughout the fluid media in the main root canal and into the lateral canals, thereby cleaning the entire root system. The use of a substantially incompressible fluid medium causes the waves produced by the photoacoustic effect to be instantly transmitted through the lateral canals. Also, since the canals are tapered in a concave fashion, the photoacoustic wave is believed to be amplified as it transverses toward the end of the lateral canals for further intensification of the destruction towards apical or cul de sac areas.

In certain embodiments of the invention, a second dissolution solution may be added to the canal after treatment with the energy source/first solution. This dissolution solution chemically dissolves and/or disintegrates any remaining nerve structure or other debris that may remain in the main canal or in any lateral canals. Preferred dissolution solutions include hypochlorite, sodium hypochlorite, perborate, calcium hydroxide, acetic acid/lubricant/doxycycline and other like nerve tissue or matrix dissolving substances such as chelating agents (EDTA) and inorganic agents such as titanium oxides.

Finally, after desired tissue has been removed from the tooth interior, the canal may be irrigated to remove any remaining debris and remaining solution, and then obturated with a material of choice, such as gutta percha, root canal resin, etc., according to standard practices in the industry.

Qualitative experimentation was performed placing a fluid into a Dampen dish located on a Formica surface. The laser applicator tip was placed into the fluid and fired repetitively.

The photoacoustic wave vibrated the Dampen dish on the Formica surface making an audible sound. For a specific tip this audible sound increased with an increasing power level of the laser. This was verified by placing a sound level meter one inch away from the Dampen dish and recording the dB level. This implies that the power level is proportional to the amplitude of the photoacoustic wave. Next, the laser power level was held constant and the tip was changed. The tapered tip and a tip with a stripped sheath produced a greater photoacoustic wave than the standard flat tip. A tapered, stripped tip was then frosted or etched. This tip was tested and showed a greater photoacoustic wave generated than the non-frosted version. This was verified to be true at three different power levels. It would appear that since the power level was held constant, the photoacoustic wave amplitude would also be proportional to the exposed area and the surface treatment.

In a quantitative investigation of the applicator tip a MEMS Pressure sensor was utilized to measure the photoacoustic wave amplitude. This testing has shown a dramatic increase in the photoacoustic wave propagation caused by changes in the geometry and texturing of the tip. The inventors have also discovered that stripping of the cladding from the end of the applicator tip results in increases in the photoacoustic wave effect. In this regard, a small plastic vial was fitted with a fluid connection that was close coupled hydraulically to a miniature MEMS piezo-resistive pressure sensor (Honeywell Model 24PCCFA6D). The sensor output was run through a differential amplifier and coupled to a digital Oscilloscope (Tektronics Model TDS 220). The vial and sensor were filled with water. Laser tips having varying applicator tip configurations were fully submerged below the fluid level in the vial and fired at a frequency of 10 HZ. The magnitude of the photoacoustic pressure waves was recorded by the pressure sensor.

A 170% increase in pressure measured from generation of the photoacoustic waves was observed for the tapered tip versus the standard blunt-ended tip. A 580% increase in pressure measured from generation of the photoacoustic wave was observed for textured (frosted) tapered tips versus the standard blunt-ended tip. Rather than emitting in a substantially linear direction, the frosting disperses the light omnidirectionally causing excitation and expansion of more fluid molecules.

An increase in photoacoustic wave generation was seen by stripping the polyamide sheath away from about 2 mm to about 10 mm from the tapered end. Although laser light is coherent and typically travels substantially in a straight line, some light bounces off of the polyamide sheath at an angle. As this light travels down the light path it continues bouncing off of the inside of the polyamide sheath and will eventually exit at an angle to the sheath once the sheath stops and exposes a non sheathed section. Therefore, some of the laser light would also exit where the polyamide sheath has been removed, upstream of the tapered tip end. A tip with the sheath removed for 2 to 10 mm directly upstream of the tapered section was placed in the above-mentioned test set up and showed markedly better production of photoacoustic waves.

In various other embodiments of the invention, energy sources other than lasers may be used to produce the photoacoustic waves including, but not limited to, other sources of light energy, sonic, ultrasonic, photo-acoustic, thermo-acoustic, micromechanical stirring, magnetic fields, electric fields, radio-frequency, and other exciter mechanisms or other similar forms that can impart energy to a solution. Some of these sources penetrate the tooth structure externally. Additional subablative energy sources may be used to create other types of pressure waves in a solution, such as chemoacoustic waves (shock waves created by rapid chemical expansion creating shock and pressure waves). Such waves can be created for example by loading the nanoparticles with a chemical that expands rapidly upon excitation, coating nanoparticles with a hard shell (e.g. polyvinyl alcohol), and activating the chemistry with an energy source such as optical, ultrasonic, radio-frequency, etc. As the activating chemical expands, pressure builds up in the hard shell, when the shell bursts it creates a shock wave that can propagate throughout the fluid similar to a photoacoustic wave. Additionally, a photoacoustic wave can be the activating energy source for producing the chemoacoustic wave.

Further, the present invention may be used for various procedures other than root canal treatment, such as for treatment of dental caries, cavities or tooth decay. Additionally, the present invention may be usable for treatments of bone and other highly networked material where infection is problematic, e.g. dental implants, bone infection, periodontal disease, vascular clotting, organ stones, scar tissues, etc. Adding a tube structure around the tip which might be perforated and will allow introduction of a fluid around the tip that will allow the photoacoustic waves to be directed into more difficult areas that do not contain fluid volume such as periodontal and gum tissue. This would be considered a type of photoacoustic transmission tube. This application process may also be used in other soft tissue applications where it is necessary to expand the diseased tissue or material to allow more rapid access and penetration to healing agents, chemicals or biologicals; i.e. antibiotics, peptides, proteins, enzymes, catalysts, genetics (DNA, mRNA or RNA or derivatives) or antibody based therapeutics or combinations thereof. In some cases, the present methodology may be used to rapidly dissolve or destroy diseased tissue areas. Additionally, the present invention may be used to expand diseased tissue in an abscess, allowing for extremely rapid and efficient penetration of healing or biological agents. The porosity created in the tissue by photoacoustic waves may allow for rapid infusion with the subsequent chemical species that can impose destruction, healing or cleaning or a combination of these events. The speed of this healing action may allow medical procedures that currently are not viable because of extensive time required for standard healing processes, i.e., sometimes adjacent tissue is infected because the original infection cannot be controlled more rapidly than the infection propagates. In this case, expanding the diseased tissue to enhance porosity may allow near instantaneous access for the medication, e.g., antibiotic or other agents.

Furthermore, the present invention may be applied to begin, construct or stage the activation of cells and/or tissues, including the area of transplantation and use in stem or primordial cells accentuation, their attachment and/or stimulation for growth and differentiation. The present invention is also believed to be usable to activate cells, e.g., progenitor, primordial or stem cells, to promote inherent nascent bone or tissue growth and differentiation, as well as in transplantation where stem or primordial cells are accentuated in their attachment and stimulated for growth and differentiation.

In one of the alternate embodiments of this invention, nanotubes or other micro-structures can be moved around in a therapeutic fluid by applying a magnetic field. An alternating or pulsed magnetic field could impart significant motion and stirring of the therapeutic fluid. Since the field would penetrate the entire tooth, the stirring action would also occur throughout the lateral or accessory canal system. These moving micro-particles would also act as an abrasive on any bacteria, virus, nerve material, or debris within the canal system. The effect would be a more thorough circulation of the fluid throughout the canal system to provide superior cleaning and debridement of the canal system. Magnetic material can also be inserted into, adsorbed onto, or absorbed into the nanotube or other microstructure increasing its magnetic moment.

TiO$_2$ or other similar compounds can be activated and made bactericidal by exposing them to UV light or by inserting them in an electric field. Once excited these can destroy bacteria and other organic compounds such as remaining nerve tissue. Such compounds can be part of a therapeutic and can be activated by a UV light source pointed toward the therapeutic fluid, a UV source dipped into the fluid, or a UV laser source. These TiO$_2$ or other similar compounds can also be activated by an alternating or pulsed electric field. One means to supply such an electric field could be by an external device that would bridge the tooth. Since the field propagates throughout the entire tooth it would also react TiO$_2$ or other similar compounds within the accessory or lateral canals. This action could also be combined with the micro-particle based motion action mentioned above. This combination would more thoroughly clean and debride the canals. Since electric fields are generated externally and penetrate the entire root structure they could be used several months or on a yearly basis after the tooth is sealed to reactivate the titanium oxide and its bactericidal properties.

The foregoing description of preferred embodiments for this disclosure has been presented for purposes of illustration and description. The disclosure is not intended to be exhaustive or to limit the various embodiments to the precise form disclosed. Other modifications or variations are possible in light of the above teachings. The embodiments are chosen and described in an effort to provide the best illustrations of the principles of the underlying concepts and their practical application, and to thereby enable one of ordinary skill in the art to utilize the various embodiments with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method for treating a root canal in a tooth containing a crown portion extending to above a gum line and an elongate root integral with and projecting from the crown into the gum and an adjacent jaw bone, the root having a root canal containing pulp including nerve and other tissue in open communication with a pulp chamber in the crown, the method comprising:

forming an opening in the crown into the pulp chamber dimensioned to enable working access to the root canal of said root for treatment thereof, removing pulp from said pulp chamber to provide an open area therein to gain access to pulp in said root canal, introducing liquid into at least said open area in said pulp chamber in an amount sufficient to provide a liquid reservoir, the upper level of which rises to an immersion level, providing a laser system containing a source of a laser light beam and an elongate optical fiber connected to said source and configured to transmit said laser light beam to a tip portion thereof, said tip portion containing a tapered tip tapering to an apex with a surrounding conical wall, substantially the entire surface of which is uncovered so that said laser light beam is emitted therefrom generally omnidirectionally, substantially completely immersing at least said tip of said laser into said liquid reservoir, and pulsing said laser source at a power level of from about 0.1 W to about 1.5 W and at a pulse duration of from about 100 nanoseconds to about 1000 microseconds, at a pulse frequency of from about 2 Hz to about 25 Hz, and for a cycle time of from about 10 to about 40 seconds, wherein at least a substantial portion of the pulp in said pulp chamber and root canal is disintegrated into pulp material in admixture in and with said liquid and removing said liquid mixture containing said pulp material from the opening in the crown, rinsing, irrigating, and disinfecting said pulp chamber and root canal so as to provide substantially clean and substantially pulp-free dentin walls lining said chamber and root canal ready for filling, obturating said pulp chamber and root canal with a suitable filling material, wherein disintegration of pulp using the laser is accomplished without generation of any significant heat in said liquid so as to avoid elevating the temperature of any of the dentin, tooth, or other adjacent tissue more than about 5° C.

2. The method of claim 1, wherein said tip is tapered convexly to an apex distally of the source.

3. The method of claim 1, wherein said tip is tapered concavely to an apex distally of the source.

4. The method of claim 1, wherein the pulse frequency is maintained constant.

5. The method of claim 1, wherein the pulse frequency is varied during each pulse cycle.

6. The method of claim 1, wherein the pulse frequency is maintained at about 15 Hz.

7. The method of claim 1, wherein the power level is maintained at about 1.5 Watts.

8. The method of claim 1, wherein the pulse duration is maintained substantially constant during each cycle at from about 50 to about 400 microseconds.

9. The method of claim 1, further comprising the step of removing at least part of the pulp from said root canal to make an opening in said root canal in flow communication with said open area in said pulp chamber prior to introducing the liquid into the open area.

10. The method of claim 1, wherein the optical fiber contains cladding in the form of a continuous sheath coating extending from the source to a terminus edge spaced proximally from said apex of said tapered tip toward said source by a distance of from about 2 mm to about 10 mm so that a surface of said optical fiber is uncovered over the entirety of said tapered tip and over any part of a cylindrical outer surface of said fiber between said terminus and the beginning of the tapered tip.

11. A method for treating a root canal in a tooth containing a crown portion extending to above a gum line and an elongate root integral with and projecting from the crown into the gum and an adjacent jaw bone, the root having a root canal containing pulp including nerve and other tissue in open communication with a pulp chamber in the crown, the method comprising:

forming an opening in the crown into the pulp chamber dimensioned to enable working access to the root canal of said root for treatment thereof, removing pulp from said pulp chamber to provide an open area therein to gain access to pulp in said root canal, introducing an aqueous solution into at least said open area in said pulp chamber in an amount sufficient to provide a liquid reservoir, the upper level of which rises to an immersion level, providing a laser system containing a source of a laser light beam and an elongate optical fiber connected to said source and configured to transmit said laser light beam to a tip portion thereof, said tip portion containing a tapered tip tapering to an apex with a surrounding conical wall, substantially the entire surface of which is uncovered so that said laser light beam is emitted therefrom generally omnidirectionally, substantially completely immersing at least said tip of said laser into said liquid reservoir, pulsing said laser source at a power level of from about 0.1 W to about 1.5 W and at a pulse duration of from about 100 nanoseconds to about 1000 microseconds, at a pulse frequency of from about 2 Hz to about 25 Hz, wherein at least a substantial portion of the pulp in said pulp chamber and root canal is disintegrated into pulp material in admixture in and with said aqueous solution, and removing said admixture containing said aqueous solution and pulp material from the opening in the crown and, rinsing, irrigating, and disinfecting said pulp chamber and root canal so as to provide substantially clean and substantially pulp-free dentin walls lining said chamber and root canal ready for filling, obturating said pulp chamber and root canal with a suitable filling material, wherein disintegration of pulp using the laser is accomplished without generation of any significant heat in said aqueous solution so as to avoid elevating the temperature of any of the dentin, tooth, or other adjacent tissue more than about 5° C.

12. A method for treating a root canal in a tooth containing a crown portion extending to above a gum line and an elongate root integral with and projecting from the crown into the gum and an adjacent jaw bone, the root having a root canal containing pulp including nerve and other tissue in open communication with a pulp chamber in the crown, the method comprising:

forming an opening in the crown into the pulp chamber dimensioned to enable working access to the root canal of said root for treatment thereof, removing pulp from said pulp chamber to provide an open area therein to gain access to pulp in said root canal, introducing an aqueous solution into at least said open area in said pulp chamber in an amount sufficient to provide a liquid reservoir, the upper level of which rises to an immersion level, providing a laser system containing a source of a laser light beam and an elongate optical fiber connected to said source and configured to transmit said laser light beam to a tip portion thereof, wherein cladding optic fiber adjacent the tip portion is spaced from about 2 mm to about 10 mm from the distal end of the tip portion, substantially the entire surface of the tip portion being uncovered so that said laser light beam is emitted therefrom generally omnidirectionally, substantially completely immersing at least said tip of said laser into said liquid reservoir, pulsing said laser source at a power level of from about 0.1 W to about 1.5 W and at a pulse duration of from about 100 nanoseconds to about 1000 microseconds, at a pulse frequency of from about 2 Hz to about 25 Hz, and for a cycle time of from about 10 to about 40 seconds, wherein at least a substantial portion of the pulp in said pulp chamber and root canal is disintegrated into pulp material in admixture in and with said aqueous solution, and removing said admixture containing said aqueous solution and pulp material from the opening in the crown, rinsing, irrigating, and disinfecting said pulp chamber and root canal so as to provide substantially clean and pulp-free dentin walls lining said chamber and root canal ready for filling, obturating said pulp chamber and root canal with a suitable filling material, wherein the disintegration of pulp using the laser is accomplished without generation of any significant heat in said aqueous solution so as to avoid elevating the temperature of any of the dentin, tooth, or other adjacent tissue more than about 5° C.

* * * * *

UNITED STATES PATENT AND TRADEMARK OFFICE
CERTIFICATE OF CORRECTION

| | | |
|---|---|---|
| PATENT NO. | : 7,980,854 B2 | |
| APPLICATION NO. | : 12/395643 | |
| DATED | : July 19, 2011 | |
| INVENTOR(S) | : Douglas L. Glover et al. | |

It is certified that error appears in the above-identified patent and that said Letters Patent is hereby corrected as shown below:

Column 1, line 4, after "continuation-in" and before "part" insert a -- - --,
Column 6, line 62, "C." should be --C--; and
Column 7, line 6, "C." should be --C--.

Column 14, line 8, after "liquid" and before "and" insert a --,--.

Signed and Sealed this
Twenty-second Day of November, 2011

David J. Kappos
*Director of the United States Patent and Trademark Office*